United States Patent
Birecki et al.

(10) Patent No.: US 9,110,007 B2
(45) Date of Patent: Aug. 18, 2015

(54) IMAGE FORMING APPARATUS HAVING OPTICAL SENSOR SYSTEM, OPTICAL SENSOR SYSTEM HAVING DETECTION MODULES, AND METHOD THEREOF

(75) Inventors: Henryk Birecki, Palo Alto, CA (US); Krzysztof Nauka, Palo Alto, CA (US); Seongsik Chang, Santa Clara, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 907 days.

(21) Appl. No.: 13/238,015

(22) Filed: Sep. 21, 2011

(65) Prior Publication Data

US 2013/0070248 A1 Mar. 21, 2013

(51) Int. Cl.
*G01N 21/59* (2006.01)
*G01N 21/27* (2006.01)
*G01N 21/3504* (2014.01)
*G01N 21/15* (2006.01)

(52) U.S. Cl.
CPC .......... *G01N 21/274* (2013.01); *G01N 21/3504* (2013.01); *G01N 2021/157* (2013.01)

(58) Field of Classification Search
CPC ................. G01N 21/3504; G01N 2021/3513; G01N 21/15; G01N 2021/155; G01N 2021/157; G01N 2021/158; G01N 21/59; G01N 21/25; G01N 21/27; G01N 21/274; G01K 12/002
USPC ........... 250/221, 222.1, 222.2, 239, 226, 573, 250/559.4, 227.25, 343, 339.12, 339.06, 250/339.09, 339.19, 341.4, 338.1, 344, 345, 250/238, 214.1; 340/601, 602, 603, 604; 356/432, 436, 437, 438, 72
See application file for complete search history.

(56) References Cited

U.S. PATENT DOCUMENTS

| | | | |
|---|---|---|---|
| 5,790,246 A * | 8/1998 | Kuhnell et al. | 356/72 |
| 7,708,947 B2 | 5/2010 | West et al. | |
| 7,804,080 B2 * | 9/2010 | Choi | 250/573 |
| 7,924,412 B2 * | 4/2011 | Chopra et al. | 356/72 |
| 7,972,865 B2 | 7/2011 | Yi et al. | |
| 8,492,722 B2 * | 7/2013 | Chang et al. | 250/339.12 |
| 8,653,439 B2 * | 2/2014 | Nauka et al. | 250/238 |
| 2008/0220535 A1 * | 9/2008 | LeBoeuf et al. | 436/164 |
| 2010/0110437 A1 * | 5/2010 | Furtaw et al. | 356/437 |
| 2011/0048106 A1 | 3/2011 | Zawacki et al. | |
| 2011/0056274 A1 * | 3/2011 | Bunod et al. | 73/40 |
| 2012/0273682 A1 * | 11/2012 | Chang et al. | 250/343 |
| 2013/0070231 A1 * | 3/2013 | Nauka et al. | 356/51 |
| 2013/0070233 A1 * | 3/2013 | Chang et al. | 356/72 |
| 2013/0070248 A1 * | 3/2013 | Birecki et al. | 356/437 |

OTHER PUBLICATIONS

"What Precautions Should I Take When Using the Hobo Pro Data Loggers Outside?", <http://www.onsetcomp.com/support/faq/what-precautions-should-i-take-when-using-hobo-pro-loggers-outside>, 2011, (no month).

(Continued)

*Primary Examiner* — John Lee
(74) *Attorney, Agent, or Firm* — HP Legal Department

(57) ABSTRACT

An optical sensor system is disclosed including a source module, a first detection module, and a second detection module. The source module includes a source housing unit having a source window member. The source module may emit a detection signal through the source window member. The first detection module and the second detection module are spaced apart from the source module.

20 Claims, 8 Drawing Sheets

(56) References Cited

OTHER PUBLICATIONS

Stewart, K.M.E; "Doped Polyaniline for Gas Sensors for the Detection of Formaldehyde", <http://uwspace.uwaterloo.ca/bitstream/10012/5852/1/Stewart_Katherine.pdf>, 2011, (no month).

Stockdale, Mark; "Minipid User Manual V1.8", <http://www.ionscience.com/assets/files/manuals/MiniPID%20Manual%203%20Pin%20V1.8.pdf>, Aug. 11, 2010.

* cited by examiner

IMAGE FORMING APPARATUS HAVING OPTICAL SENSOR SYSTEM, OPTICAL SENSOR SYSTEM HAVING DETECTION MODULES, AND METHOD THEREOF

CROSS REFERENCE TO RELATED APPLICATIONS

This application is related to commonly-owned patent application Ser. No. 13/238,281, entitled "IMAGE FORMING APPARATUS HAVING OPTICAL SENSOR SYSTEM, OPTICAL SENSOR SYSTEM HAVING SHIELDS, AND METHOD THEREOF" and filed contemporaneously herewith by Seongsik Chang, Henryk Birecki, and Krzysztof Nauka, and Ser. No. 13/238,001, entitled "IMAGE FORMING APPARATUS HAVING OPTICAL SENSOR SYSTEM, OPTICAL SENSOR SYSTEM HAVING HEATING MODULE, AND METHOD THEREOF" and filed contemporaneously herewith by Krzysztof Nauka, Seongsik Chang, and Henryk Birecki, the latter which has issued as U.S. Pat. No. 8,653,439 on Feb. 18, 2014, and which related applications are incorporated herein by reference in their entirety.

BACKGROUND

Optical sensor systems may include source modules and detection modules to detect the presence of objects there between. The source modules and detection modules may include respective window members. The source module may emit a detection signal such as an infrared signal through the respective window members to be received by a detection module. The objects such as volatile organic compounds (VOC) may be detected when present in a path of the detection signal. Such optical sensor systems may be included in image forming apparatuses, air quality monitoring devices, or the like.

BRIEF DESCRIPTION OF THE DRAWINGS

Non-limiting examples of the present disclosure are described in the following description, read with reference to the figures attached hereto and do not limit the scope of the claims. In the figures, identical and similar structures, elements or parts thereof that appear in more than one figure are generally labeled with the same or similar references in the figures in which they appear. Dimensions of components and features illustrated in the figures are chosen primarily for convenience and clarity of presentation and are not necessarily to scale. Referring to the attached figures:

DETAILED DESCRIPTION

Figure 1:
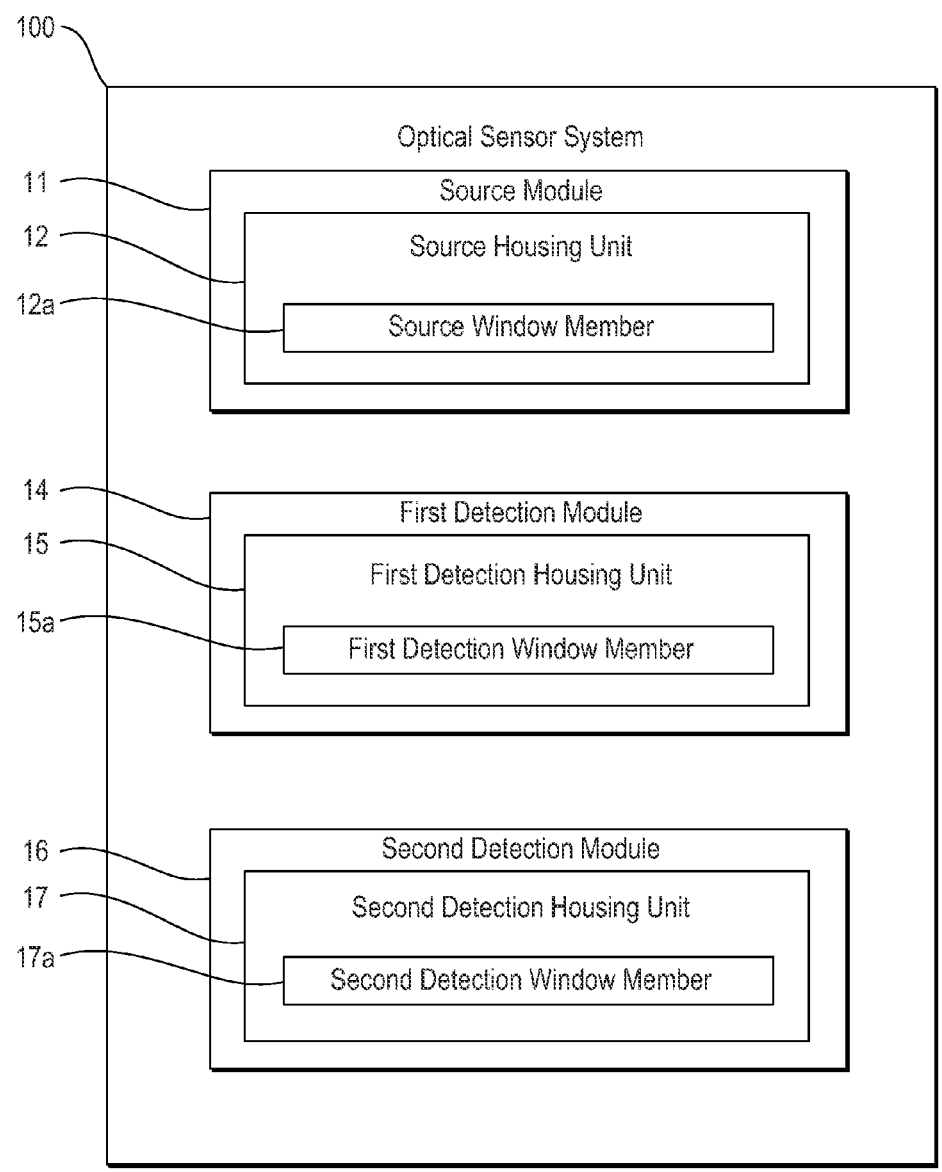
FIG. 1 is a block diagram illustrating an optical sensor system according to an example.

In the following detailed description, reference is made to the accompanying drawings which form a part hereof, and in which is depicted by way of illustration specific examples in which the present disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims.

Optical sensor systems may include source modules and detection modules to detect the presence of objects there between such as volatile organic compounds (VOC). For example, VOC may be in a form of a gas, liquid and/or solid and include organic compounds that may easily become vapor or gaseous. An optical sensor system may detect VOC in a form of a gas in a volume of air between a source module and a detection module, for example, to be used as a basis for determining a total amount of VOC in a form of a gas present in an environment. Such information may be used to provide alerts based on VOC concentration and/or activate processes to reduce VOC concentration. The source modules may include a source window member. The source module may emit a detection signal such as an infrared signal through the source window member to be received by a detection module through a detection window member thereof. The objects, for example, such as VOC may be detected when present in a path of the detection signal between the source module and detection module. Such optical sensor systems may be included in image forming apparatuses, air quality monitoring devices, or the like. The Image forming apparatuses may include liquid electrophotography printing apparatuses to form images on an image transfer blanket that, subsequently, get transferred to media.

Unwanted deposits in a form of solid and/or liquid buildup such as VOC deposits, however, may form on the source window member and the detection window member. The deposits may decrease transmission of the detection signal through the respective window members, for example, by promoting scattering due to non-uniformity of the thickness of the deposits. That is, infrared light inside and outside of a VOC absorption band may be scattered off of solid or liquid deposit formations on the respective window members. Consequently, without reducing and/or compensating for deposit formations, the detection signal may be degraded and/or potentially distort detection of objects such as the VOC in the form of a gas present in the path of the detection signal between the source and detection modules resulting in incorrect VOC reading by the detection module.

In examples, the optical sensor system may include a source module to emit a detection signal. The optical sensor system may also include first and second detection modules to receive the detection signal. The source module, the first detection module and the second detection module may include respective window members to suppress deleterious effects distorting transmission of the detection signal between the source module and the first detection module. For example, heating of the respective window members to suppress the deleterious effects distorting transmission of the detection signal caused by deposit formation of objects on respective window members may be activated in response to the second detection module sensing degradation of the detection signal.

In examples, an optical sensor system includes, amongst other things, a source module, a first detection module, and a second detection module. The source module includes a source housing unit having a source window member. The source module may emit a detection signal through the source window member. The first detection module includes a first detection housing unit having a first detection window member. The second detection module includes a second detection housing unit including a second detection window member. The first detection module may receive the detection signal to determine an amount of VOC present in the path of the detection signal between the source module and the first detection module. The second detection module may receive the detection signal to determine deposit formation of the VOC on the source window member and the second detection window member.

FIG. 1 is a block diagram illustrating an optical sensor system apparatus according to an example. Referring to FIG. 1, in some examples, an optical sensor system 100 includes a source module 11, a first detection module 14 and a second detection module 16. The source module 11 includes a source housing unit 12 having a source window member 12a. The source module 11 may emit a detection signal through the source window member 12a. In some examples, the first detection module 14 may include a first detection housing unit 15 having a first detection window member 15a. The first detection module 14 may be spaced apart from the source module 11 to receive the detection signal to determine an amount of VOC present in the path of the detection signal between the source module 11 and the first detection module 14. The second detection module 16 may include a second detection housing unit 17 including a second detection window member 17a. The second detection module 16 may be spaced apart from the source module 11 to receive the detection signal to determine at least one of a presence and an amount of deposit formation of the VOC on the source window member 12a and the second detection window member 17a.

Figure 2A:
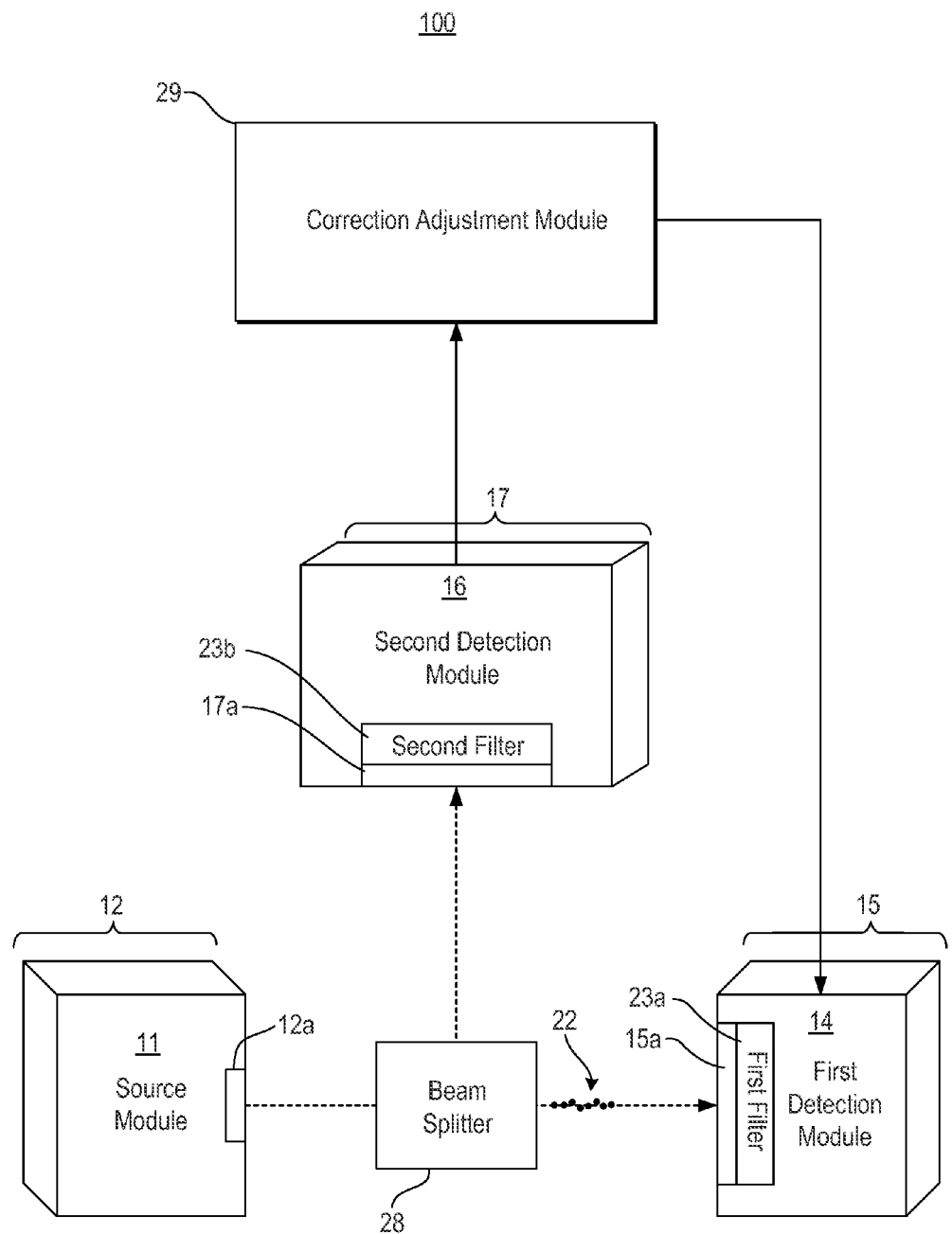
FIGS. 2A and 2B are schematic views illustrating the optical sensor system of FIG. 1 according to examples.
Figure 2B:
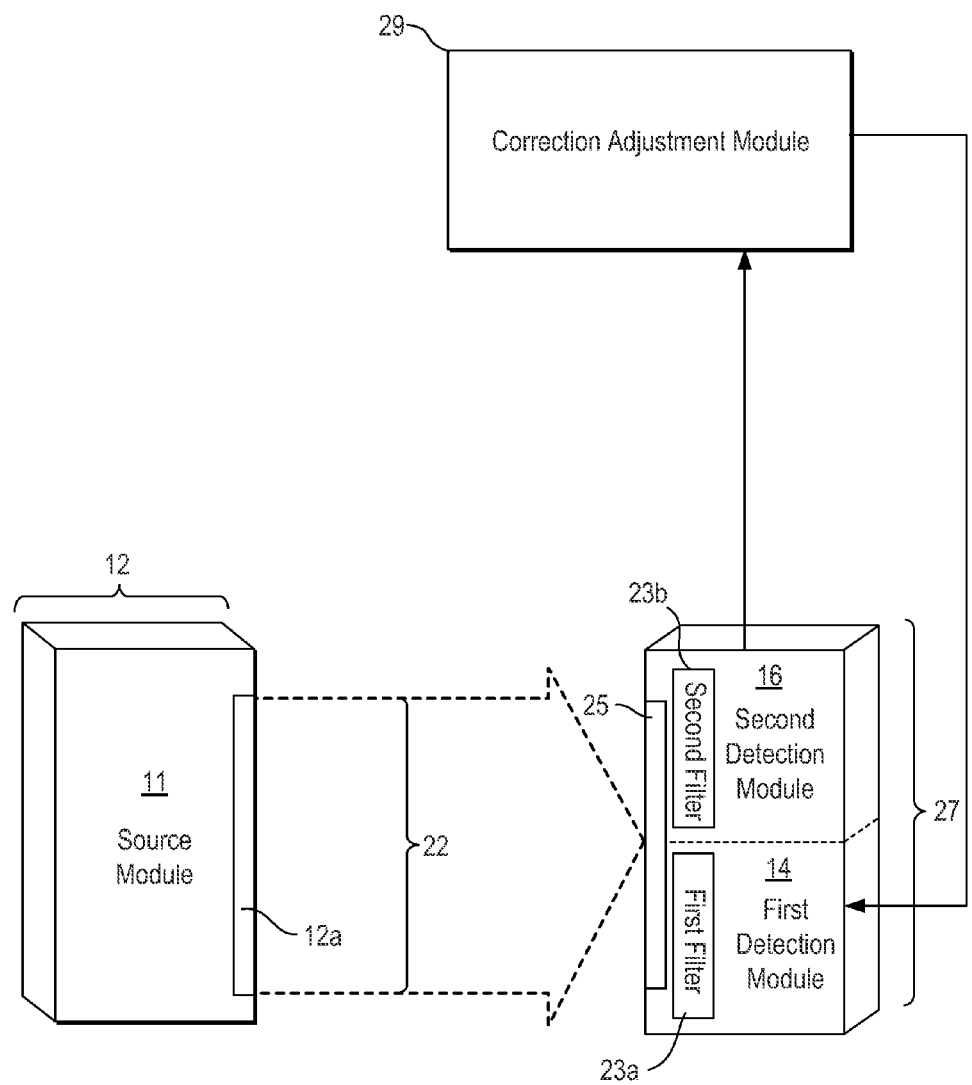

FIGS. 2A and 2B are schematic views of the optical sensor system of FIG. 1 according to examples. In some examples, the optical sensor system 100 may also include a beam splitter 28, or the like, to direct the detection signal emitted by the source module 11 to the first detection unit 14 and the second detection unit 16 as illustrated in FIG. 2A. The beam splitter 28 may allow the first and second detection modules 14 and 16 to simultaneous receive the detection signal. Alternatively, the optical sensor system 100 may include a scanning mirror (not illustrated) to sequentially direct the detection signal emitted from the source module 11 to the first and second detection modules 14 and 16. That is, the scanning mirror may rotate to change its orientation with respect to the source module 11, the first detection module 14 and the second detection module 16 to enable the detection signal to be sequentially received by the first detection module 14 and the second detection module 16.

Referring to FIG. 2A, in some examples, the first detection module 14 may also include a first filter 23a to filter the detection signal to output a first signal having a first predetermined frequency range corresponding to the amount of the VOC present in the detection signal and the amount of deposit formation of the VOC on the source window member 12a and the first detection window member 15a. For example, the first filter 23a may include a first narrow bandpass filter in which the first predetermined frequency range corresponds to a wavenumber range from 2800 $cm^{-1}$ to 3000 $cm^{-1}$. That is, the first predetermined frequency range may correspond to the frequency range in which signal absorption specific to the sensed objects such as VOC occurs.

The second detection module 16 may also include a second filter 23b to filter the detection signal to output a second signal having a second predetermined frequency range corresponding to the amount of deposit formation of the VOC on the source window member 12a and the second detection window member 17a. For example, the second filter 23b may include a second narrow bandpass filter in which the second predetermined frequency range corresponds to a wavenumber range outside the first predetermined frequency range. That is, the second predetermined frequency range may correspond to a frequency range outside the absorption band specific to the sensed objects such as VOC.

In some examples, the first detection module 14 and the second detection module 16 may be disposed in separate detection housing units 15 and 17 as illustrated in FIG. 2A. Alternatively, the first detection module 14 and the second detection module 16 may be integrated into a single integrated detection housing unit 27 as illustrated in FIG. 2B. That is, the first detection module 14 and the second detection module 16 may be disposed in the same housing unit 27 and share a common detection window member 25.

Referring to FIG. 2A, in some examples, the optical sensor system 100 may also include a correction adjustment module 29 to determine a correction adjustment parameter based on the determination of the second detection module 16. The correction adjustment module 29 may use the amount of deposit formation of the VOC on the source window member 12a and the second detection window member 17a determined by the second detection module 16 to obtain the correction adjustment parameter. Thus, the correction adjustment parameter may correspond to a value that quantifies an amount of distortion of the detection signal received by the first detection module 14 due to unwanted deposit formation on respective window members. Thus, the correction adjustment parameter may be applied to the first signal, for example, by the first detection module 14, to form an adjusted first signal corresponding to the amount of the VOC in a form of gas present in the path of the detection signal as it is received by the first detection module 14. That is, the first detection module 14 may determine the amount of the VOC in the form of gas in the path of the detection signal based on an adjusted first signal formed by application of the correction adjustment parameter to the first signal.

Referring to FIG. 2B, in some examples, an integrated detection housing unit 27 may include a first detection module 14, a second detection module 16, a first filter 23a, a second filter 23b, and a detection window member 25. The detection window member 25 may pass through the detection signal to the first filter 23a and the second filter 23b. The first filter 23a may filter the detection signal to output a first filtered signal to the first detection module 14 having a first predetermined frequency range corresponding to the amount of the VOC present in the detection signal and the amount of deposit formation of the VOC on the source window member 12a and the detection window member 25. For example, the first filter 23a may include a first narrow bandpass filter in which the first predetermined frequency range corresponds to a wavenumber range from 2800 $cm^{-1}$ to 3000 $cm^{-1}$. That is, the first predetermined frequency range may correspond to the frequency range in which signal absorption specific to the sensed objects such as VOC occurs.

The second filter 23b may filter the detection signal to output a second filtered signal to the second detection module 16 having a second predetermined frequency range corresponding to the amount of deposit formation of the VOC on the source window member 12a and the detection window member 25. For example, the second filter 23b may include a second narrow bandpass filter in which the second predetermined frequency range corresponds to a wavenumber range outside the first predetermined frequency range. That is, the second predetermined frequency range may correspond to a frequency range outside the absorption band specific to the sensed objects such as VOC.

Referring to FIG. 2B, in some examples, the optical sensor system 100 may also include a correction adjustment module 29 to determine a correction adjustment parameter based on the determination of the second detection module 16. The correction adjustment module 29 may use the amount of deposit formation of the VOC on the source window member 12a and the detection window member 25 determined by the second detection module 16 to obtain the correction adjustment parameter. Thus, the correction adjustment parameter may correspond to a value that quantifies an amount of distortion of the detection signal received by the first detection module 14 due to unwanted deposit formation on respective window members 12a and 25. Thus, the correction adjustment parameter may be applied to the first signal, for example, by the first detection module 14, to form an adjusted first signal corresponding to the amount of the VOC in the form of gas present in the path of the detection signal as it is received by the first detection module 14. That is, the first detection module 14 may determine the amount of the VOC in the path of the detection signal based on an adjusted first signal formed by application of the correction adjustment parameter to the first signal.

Figure 3:
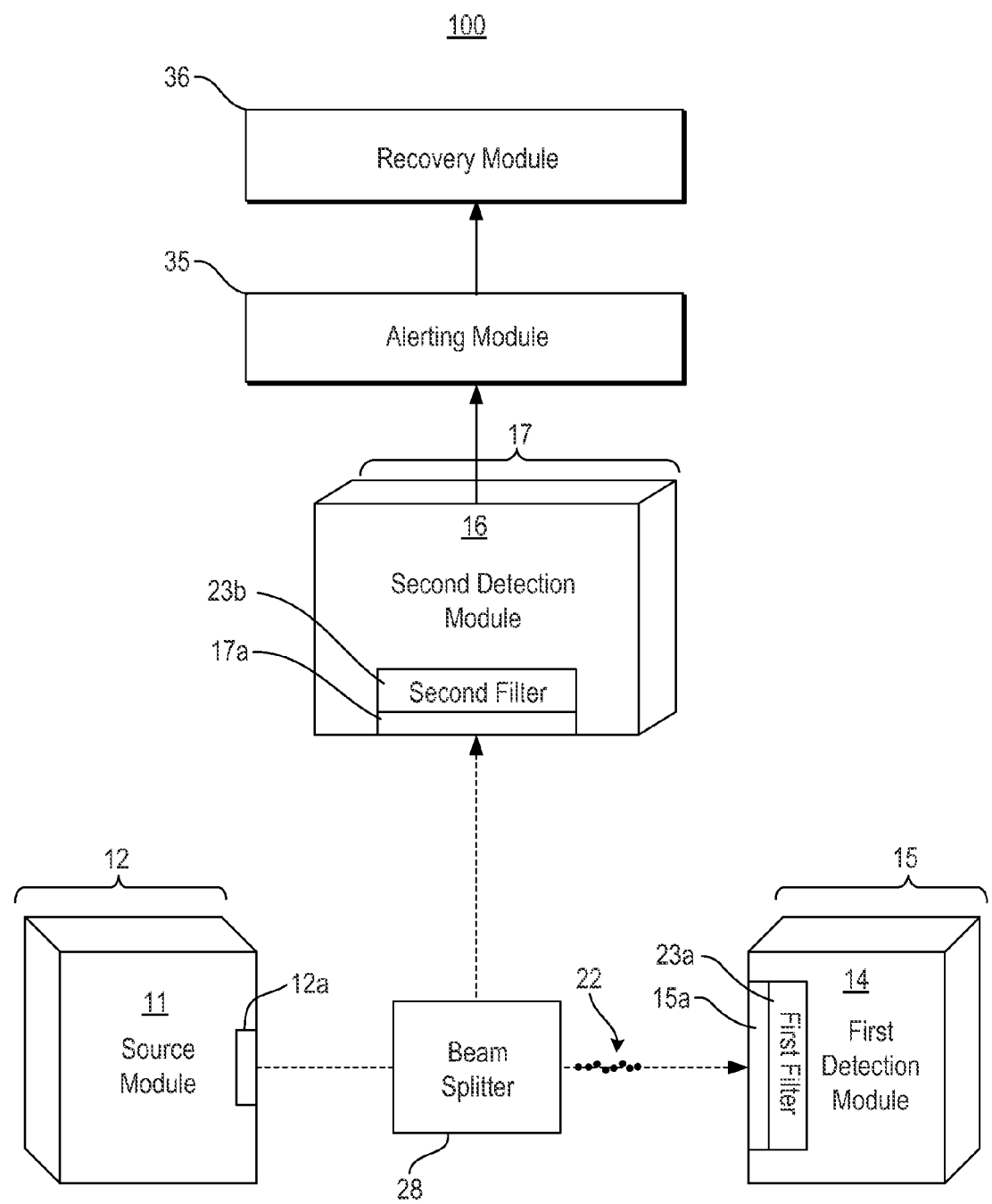
FIG. 3 is a schematic view illustrating the optical sensor system of FIG. 1 according to an example.

FIG. 3 is a schematic view illustrating the optical sensor system of FIG. 1 according to an example. Referring to FIG. 3, the optical sensor system 100 of FIG. 1 may also include at least one of an alerting module 35 to alert a user of a system malfunction such as unreliable VOC readings due to unwanted deposition formations and a recovery module 36 to perform a recovery action to correct the system malfunction in response to a determination of the presence of the deposit formation of the VOC on the source window member 12a and the second detection window member 17a. For example, the alerting module 35 may include a speaker, a light, a message on a display, or the like. For example, the recovery module 36 may be a deposit removal device such as a wiper to contact and remove respective deposit formations of the respective window members 12a and 17a, a heating module to vaporize the respective deposit formations of the respective window members 12a and 17a, or the like.

In some examples, the source module 11, the first detection module 14, the second detection module 16, the correction adjustment module 29, the alerting module 35, and/or the recovery module 36 may be implemented in hardware, software, or in a combination of hardware and software. In some examples, the source module 12a, the first detection module 14, the second detection module 16, the correction adjustment module 29, the alerting module 35, and/or the recovery module 36 may be implemented in part as a computer program such as a set of machine-readable instructions stored in the optical sensor system 100 locally or remotely. For example, the computer program may be stored in a memory such as a server or a host computing device considered herein as part of the optical sensor system 100.

Figure 4:
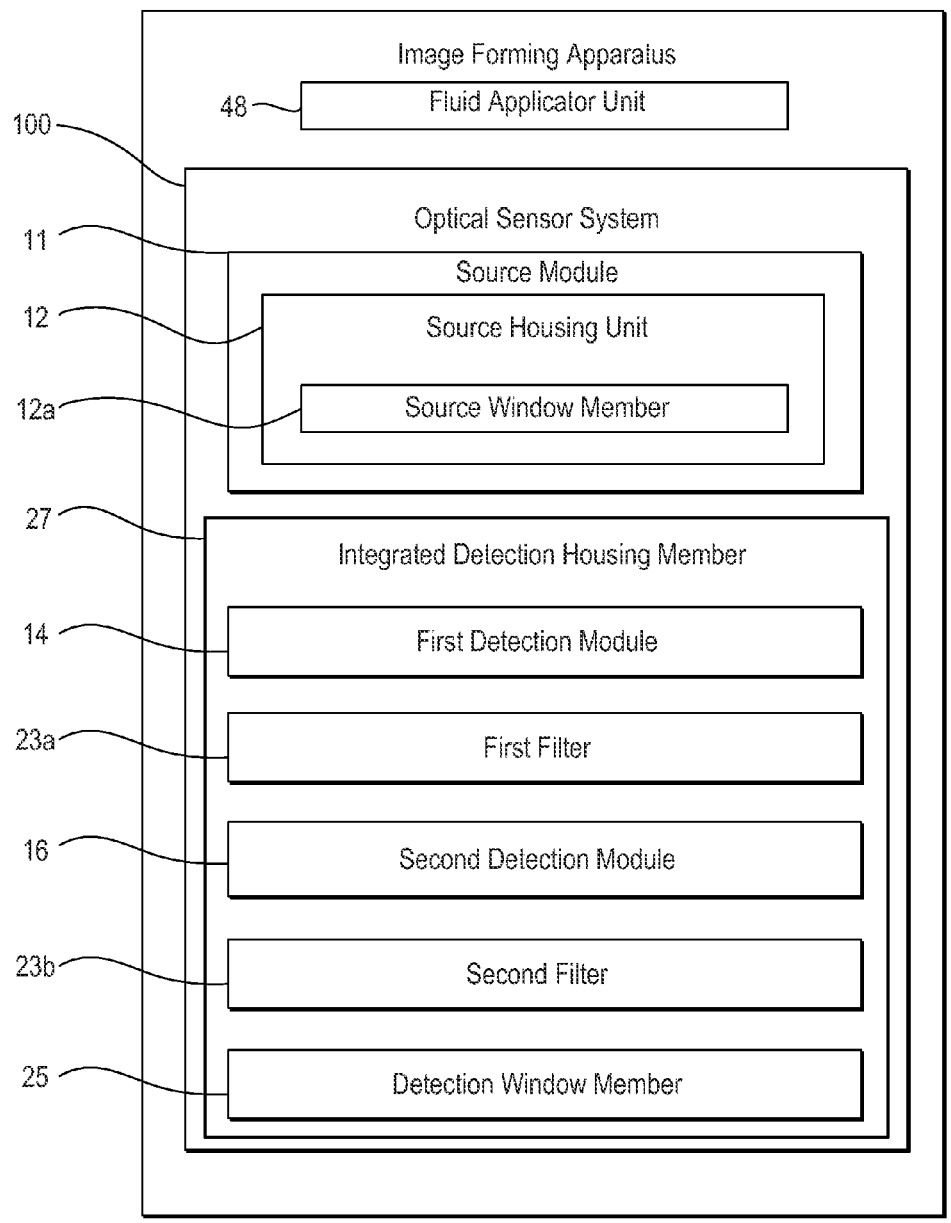
FIG. 4 is a block diagram illustrating an image forming apparatus including an optical sensor system according to an example.

FIG. 4 is a block diagram illustrating an image forming apparatus including an optical sensor system according to an example. In some examples, the image forming apparatus 400 may include a liquid electrophotograpy printing apparatus that forms images on media by applying fluid onto an image transfer blanket of an intermediate transfer member and, subsequently, onto the media. For example, the fluid may include ink such as liquid toner, for example, ElectroInk, trademarked by Hewlett-Packard Company including imaging oil, for example, Isopar trademarked by Exxon Corporation. Referring to FIG. 4, in some examples, the image forming apparatus 400 includes a fluid applicator unit 48 and an optical sensor system 100. The fluid applicator unit 48 may apply fluid to an object such as an image transfer blanket or a media to form an image. For example, the fluid applicator unit 48 may include an inkjet print head, a binary developer unit, or the like.

Referring to FIG. 4, in some examples, the optical sensor system 100 may detect VOC formed from the fluid applied by the fluid applicator unit 48. The optical sensor system 100 may include a source module 11, an integrated detection housing unit 27 including a first detection module 14, a second detection module 16, a first filter 23a, a second filter 23b, and a detection window member 25. The source module 11 may include a source housing unit 12 having a source window member 12a. The source module 11 may emit a detection signal through the source window member 12a to detect the VOC 22 present in the path of the detection signal between the source module 11 and the first detection module 14.

The detection window member 25 may be spaced apart from the source module 11 to pass through the detection signal to the first detection module 14 through the first filter 23a and the second detection module 16 through the second filter 23b. The first filter 23a may filter the detection signal and provide a first filtered signal to the first detection module 14. The first detection module 14 may determine an amount of VOC present in a path of the detection signal between the source module 11 and the first detection module 14 based on the first filtered signal. The second filter 23b may filter the detection signal and provide a second filtered signal to the second detection module 16. The second detection module 16 may receive the detection signal to determine at least one of a presence and the amount of deposit formation of the VOC on the source window member 11 and the detection window member 25 based on the second filtered signal.

In some examples, the first filtered signal includes a first predetermined frequency range corresponding to the amount of the VOC present in the detection signal and the amount of deposit formation of the VOC on the source window member 12a and the detection window member 25. The second filtered signal may include a second predetermined frequency range corresponding to the amount of deposit formation of the VOC on the source window member 12a and the detection window member 25. The first filter 23a may include a first narrow bandpass filter such that the first predetermined frequency range corresponds to a wavenumber range from 2800 $cm^{-1}$ to 3000 $cm^{-1}$ and the second filter 23b includes a second narrow bandpass filter such that the second predetermined frequency range corresponds to a wavenumber range outside the first predetermined frequency range.

In some examples, the image forming apparatus 100 may also include a correction adjustment module 29 to determine a correction adjustment parameter based on the determination of the second detection module 16. The first detection module 14 may determine the amount of VOC in the form of gas in the path of the detection signal based on an adjusted first signal formed by application of the correction adjustment parameter to the first signal. The image forming apparatus 100 may also include a beam splitter 28 disposed inside the integrated detection housing unit 27 to direct the detection signal emitted from the source module 11 to the first filter 23a and the second filter 23b.

Figure 5:
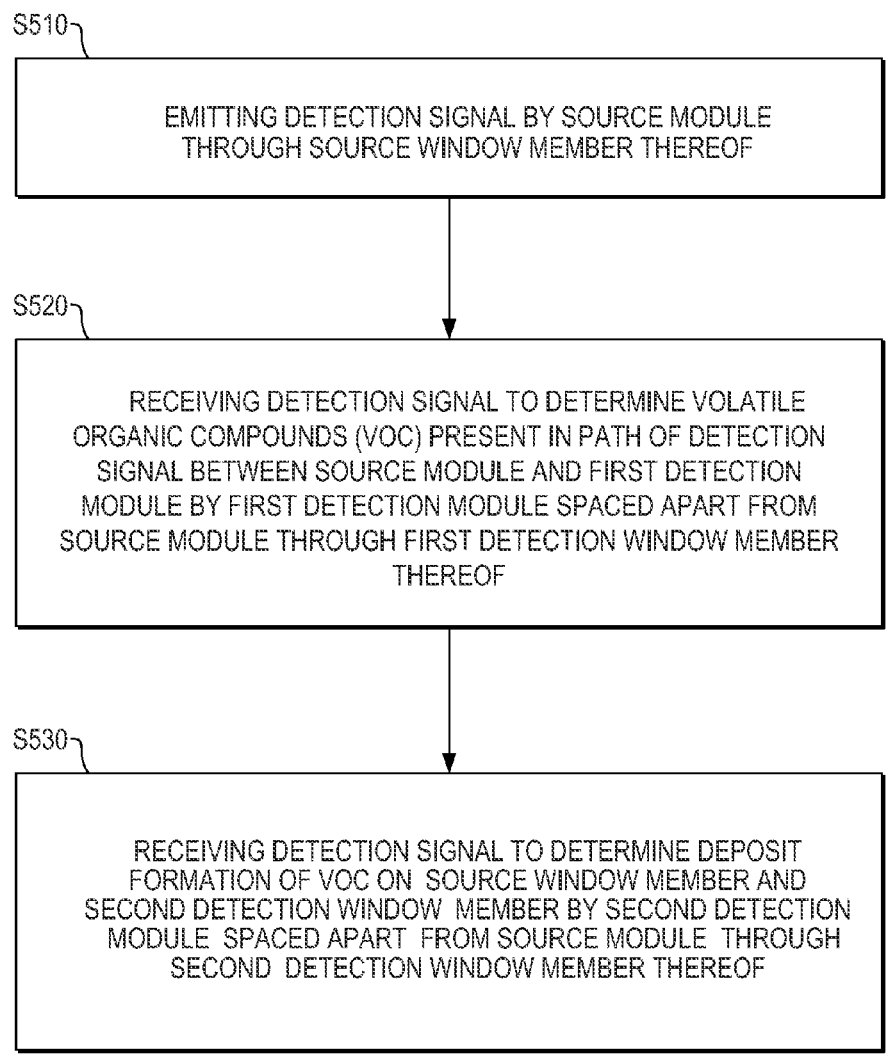
FIG. 5 is a flowchart illustrating a method of detecting volatile organic compounds according to an example.

FIG. 5 is a flowchart illustrating a method of detecting volatile organic compounds according to an example. Referring to FIG. 5, in block S510, a detection signal is emitted by a source module through a source window member thereof. In block S520, the detection signal to determine an amount of VOC present in the detection signal between the source module and the first detection module is received by a first detection module spaced apart from the source module through a first detection window member thereof. In block S530, the detection signal to determine deposit formation of the VOC on the source window member and the second detection window member is received by a second detection module spaced apart from the source module through a second detection window member thereof.

In some examples, the method may also include filtering the detection signal by a first filter of the first detection module to output a first signal having a first predetermined frequency range. The first predetermined frequency range may correspond to the amount of the VOC present in the detection signal and the amount of deposit formation of the VOC on the source window member and the first detection window member. For example, the first filter may include a first narrow bandpass filter in which the first predetermined frequency range corresponds to a wavenumber range from 2800 cm$^{-1}$ to 3000 cm$^{-1}$. The method may also include filtering the detection signal by a second filter of the second detection module to output a second signal having a second predetermined frequency range. The second predetermined frequency range may correspond to the amount of deposit formation of the VOC on the source window member and the second detection window member. For example, the second filter may include a second narrow bandpass filter in which the second predetermined frequency range corresponds to a wavenumber range outside the first predetermined frequency range. The method may also include determining a correction adjustment parameter by a correction adjustment module based on the determination of the second detection module. Additionally, the method may also include determining the amount of VOC in the form of gas in the path of the detection signal by the first detection module based on an adjusted first signal formed by application of the correction adjustment parameter to the first signal.

Figure 6:
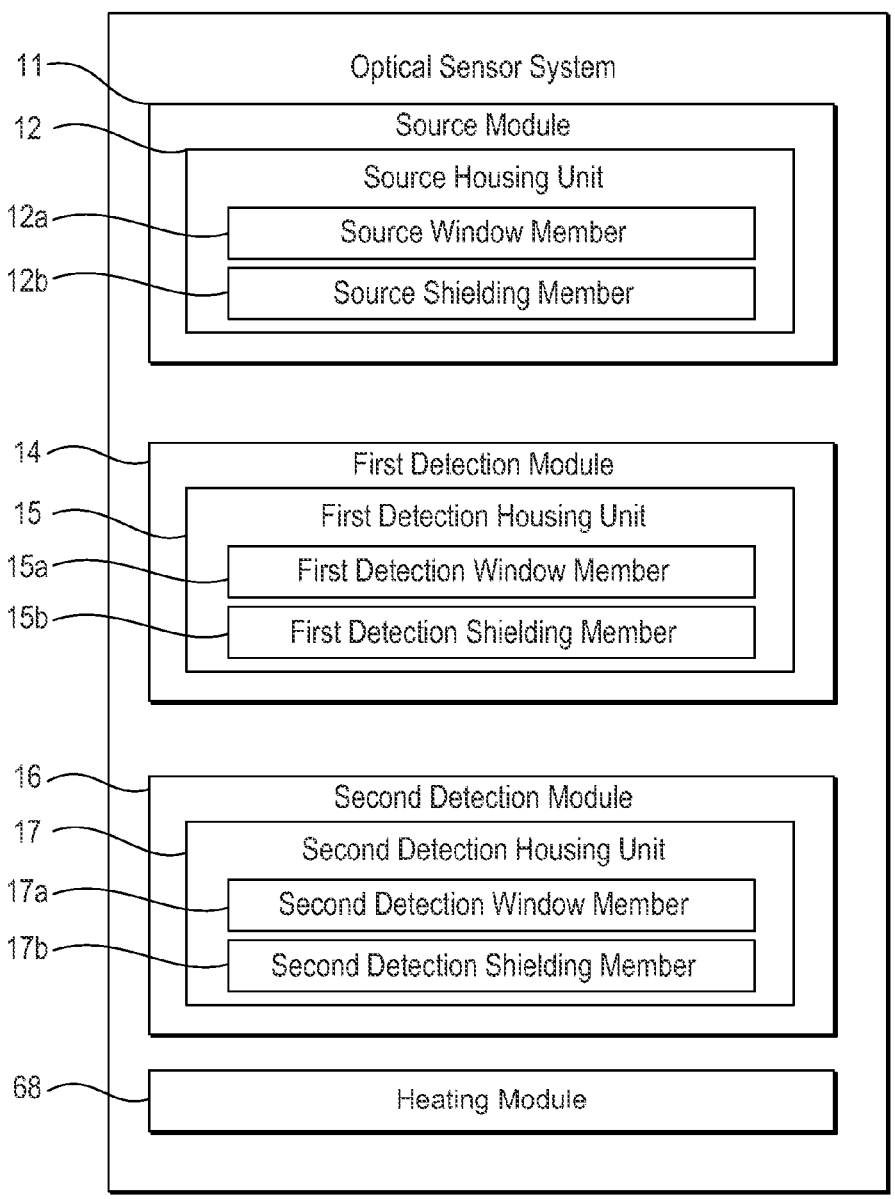
FIG. 6 is a block diagram illustrating an optical sensor system according to an example.
Figure 7:
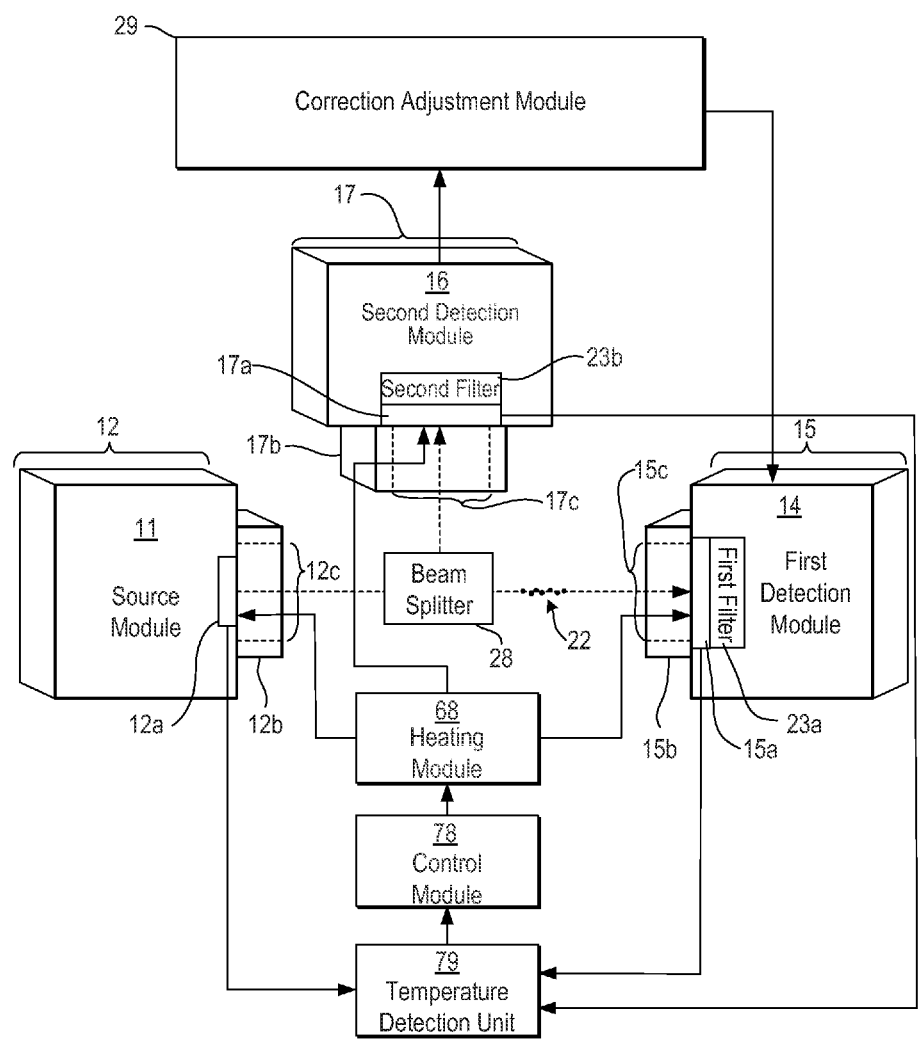
FIG. 7 is a schematic diagram illustrating the optical sensor system of FIG. 6 according to an example.

FIG. 6 is a block diagram illustrating an optical system according to an example. FIG. 7 is a schematic view of the optical sensor system of FIG. 6 according to an example. Referring to FIGS. 6-7, in some examples, an optical sensor system 100 includes a source module 11, a first detection module 14, a second detection module 16, and a heating module 68. The source module 11 may include a source housing unit 12 and emit a detection signal through the source window member 12a. The source housing unit 12 may include a source window member 12a and a source shielding member 12b having a respective longitudinal opening 12c there through (FIG. 7). The source shielding member 12b may surround the source window member 12a to reduce deposit formation of VOC on the source window member 12a.

Referring to FIGS. 6-7, in some examples, the first detection module 14 may be spaced apart from the source module 11. The first detection module 14 may receive the detection signal to determine an amount of the VOC 22 present in the path of the detection signal between the source module 11 and the first detection module 14. In some examples, the first detection module 14 may include a first housing unit 12 and a first filter 23a therein. The first filter 23a may filter the detection signal to output a first signal having a first predetermined frequency range. The first predetermined frequency range may correspond to the amount of the VOC present in the path of the detection signal and the amount of deposit formation of the VOC on the source window member 12a and the first detection window member 15a.

For example, the first filter 23a may include a first narrow bandpass filter in which the first predetermined frequency range corresponds to a wavenumber range from 2800 cm$^{-1}$ to 3000 cm$^{-1}$. The first detection housing unit 15 may include a first detection window member 15a and a first detection shielding member 15b having a respective longitudinal opening 15c there through (FIG. 7). The first detection shielding member 15b may surround the first detection window member 15a to reduce deposit formation of the VOC on the first detection window member 15a.

Referring to FIGS. 6-7, in some examples, the second detection module 16 may be spaced apart from the source module 11 to receive the detection signal to determine at least one of a presence and an amount of deposit formation of the VOC on the source window member 12a and the second detection window member 17a. The second detection module 16 may include a second detection housing unit 17 and a second filter 23b therein. The second filter 23b may filter the detection signal to output a second signal having a second predetermined frequency range. The second predetermined frequency range may correspond to the amount of deposit formation of the VOC on the source window member 12a and the second detection window member 17a.

For example, the second filter 23b may include a second narrow bandpass filter such that the second predetermined frequency range corresponds to a wavenumber range outside the first predetermined frequency range. The second detection housing unit 17 may include a second detection window member 17a and a second detection shielding member 17b having a respective longitudinal opening 17c (FIG. 7) there through. The second detection shielding member 17b may surround the second detection window member 17a to reduce deposit formation of the VOC on the second detection window member 17a. The heating module 68 may heat the source window member 12a, the first detection window member 15a, and the second detection window member 17a to remove deposit formation of the VOC there from.

Referring to FIGS. 6-7, in some examples, the optical sensor system 100 may also include a temperature detection unit 79, a control module 78 and a correction adjustment module 29. The temperature detection unit 79 may detect a respective temperature of the source window member 12a, the first detection window member 15a, and the second detection window member 17a. The control module 78 may control the heating module 68 based on at least one of detection by the second detection module 16 and a respective detection by the temperature detection unit 79. For example, the second detection module 16 may detect the VOC present on the source window member 12a and the second detection window member 17a. The correction adjustment module 29 may determine a correction adjustment parameter based on a determination of the second detection module 16 corresponding to an amount of deposit formation on the source window member 12a and the second detection window member 17a as previously disclosed with respect to FIGS. 1-3.

In some examples, the control module 78 may control at least one of the heating module 68, the source module 11, and the respective detection modules 14 and 16 so that VOC detection is not active while the heating module 68 is active. The control module 78 may control the heating module 68 based on a determination of an amount of deposit formation of the VOC on the source window member 12a and the second detection window member 17a, selectively activate and deactivate the heating module 68 for a predetermined period of time to correspond to an amount of time to maintain the respective window members 12a, 15a, and 17a in a predetermined temperature range, activate the heating module 68 to heat the respective window members 12a and 15a during the detection of the amount of VOC in the path of the detection signal, and activate the heating module 68 periodically as deemed necessary, or the like.

In some examples, the source module 11, the first detection module 14, the second detection module 16, the correction adjustment module 29, the heating module 68, the temperature detection unit 79, and/or the control module 78 may be implemented in hardware, or in a combination of hardware and software. In some examples, the source module 11, the first detection module 14, the second detection module 16, the correction adjustment module 29, the heating module 68, the temperature detection unit 79, and/or the control module 78 may be implemented in part as a computer program such as a set of machine-readable instructions stored in the optical sensor system 100 locally or remotely. For example, the computer program may be stored in a memory such as a server or a host computing device considered herein as part of the optical sensor system 100.

It is to be understood that the flowchart of FIG. 5 illustrates an architecture, functionality, and operation of an example of the present disclosure. If embodied in software, each block may represent a module, segment, or portion of code that includes one or more executable instructions to implement the specified logical function(s). If embodied in hardware, each block may represent a circuit or a number of interconnected circuits to implement the specified logical function(s). Although the flowchart of FIG. 5 illustrates a specific order of execution, the order of execution may differ from that which is depicted. For example, the order of execution of two or more blocks may be scrambled relative to the order illustrated. Also, two or more blocks illustrated in succession in FIG. 5 may be executed concurrently or with partial concurrence. All such variations are within the scope of the present disclosure.

The present disclosure has been described using non-limiting detailed descriptions of examples thereof and is not intended to limit the scope of the present disclosure. It should be understood that features and/or operations described with respect to one example may be used with other examples and that not all examples of the present disclosure have all of the features and/or operations illustrated in a particular figure or described with respect to one of the examples. Variations of examples described will occur to persons of the art. Furthermore, the terms "comprise," "include," "have" and their conjugates, shall mean, when used in the present disclosure and/or claims, "including but not necessarily limited to."

It is noted that some of the above described examples may include structure, acts or details of structures and acts that may not be essential to the present disclosure and are intended to be exemplary. Structure and acts described herein are replaceable by equivalents, which perform the same function, even if the structure or acts are different, as known in the art. Therefore, the scope of the present disclosure is limited only by the elements and limitations as used in the claims.

What is claimed is:

1. An optical sensor system, comprising:
   a source module including a source housing unit having a source window member, the source module to emit a detection signal through the source window member;
   a first detection module including a first detection housing unit having a first detection window member, the first detection module spaced apart from the source module to receive the detection signal to determine an amount of volatile organic compounds (VOC) present in a path of the detection signal between the source module and the first detection module; and
   a second detection module including a second detection housing unit including a second detection window member, the second detection module spaced apart from the source module to receive the detection signal to determine at least one of a presence and the amount of deposit formation of the VOC on the source window member and the second detection window member.

2. The optical sensor system according to claim 1, wherein the first detection module further comprises:
   a first filter to filter the detection signal to output a first signal having a first predetermined frequency range corresponding to the amount of the VOC present in the path of the detection signal and the amount of deposit formation of the VOC on the source window member and the first detection window member.

3. The optical sensor system according to claim 2, wherein the second detection module further comprises:
   a second filter to filter the detection signal to output a second signal having a second predetermined frequency range corresponding to the amount of deposit formation of the VOC on the source window member and the second detection window member.

4. The optical sensor system according to claim 3, wherein the first filter comprises a first narrow bandpass filter such that the first predetermined frequency range corresponds to a wavenumber range from 2800 $cm^{-1}$ to 3000 $cm^{-1}$ and the second filter comprises a second narrow bandpass filter such that the second predetermined frequency range corresponds to a wavenumber range outside the first predetermined frequency range.

5. The optical sensor system according to claim 3, further comprising:
   a correction adjustment module to determine a correction adjustment parameter based on the determination of the second detection module; and
   wherein the first detection module determines the amount of VOC in a form of gas in the path of the detection signal based on an adjusted first signal formed by application of the correction adjustment parameter to the first signal.

6. The optical sensor system according to claim 1, further comprising:
   at least one of a beam splitter and a scanning mirror to direct the detection signal emitted from the source module to the first detection module and the second detection module; and
   wherein the first detection module and the second detection module are one of integrated into a single detection housing unit and disposed in separate detection housing units.

7. The optical sensor system according to claim 1, further comprising:
   at least one of an alerting module to alert a user of a system malfunction and a recovery module to perform an action to correct system malfunction in response to a determination of the presence of the deposit formation of the VOC on the source window member and the second detection window member.

8. An image forming apparatus, comprising:
   a fluid applicator unit to apply fluid to an object to form an image; and
   an optical sensor system to detect volatile organic compounds (VOC) formed from the fluid applied by the fluid applicator unit, the optical sensor system including:
      a source module including a source housing unit having a source window member, the source module to emit a detection signal through the source window member;

an integrated detection housing unit including a first detection module, a first filter, a second detection module, a second filter and a detection window member spaced apart from the source module to pass through the detection signal to the first detection module through the first filter and the second detection module through the second filter;

the first filter to filter the detection signal and provide a first filtered signal to the first detection module;

the first detection module to determine an amount of VOC present in a path of the detection signal between the source module and the first detection module based on the first filtered signal, the second filter to filter the detection signal and provide a second filtered signal to the second detection module; and a second detection module to receive the detection signal to determine at least one of a presence and the amount of deposit formation of the VOC on the source window member and the detection window member based on the second filtered signal.

9. The image forming apparatus according to claim 8, wherein the first filtered signal includes a first predetermined frequency range corresponding to the amount of the VOC present in the path of the detection signal and the amount of deposit formation of the VOC on the source window member and the detection window member and the second filtered signal includes a second predetermined frequency range corresponding to the amount of deposit formation of the VOC on the source window member and the detection window member.

10. The image forming apparatus according to claim 9, wherein the first filter comprises a first narrow bandpass filter such that the first predetermined frequency range corresponds to a wavenumber range from 2800 cm$^{-1}$ to 3000 cm$^{-1}$ and the second filter comprises a second narrow bandpass filter such that the second predetermined frequency range corresponds to a wavenumber range outside the first predetermined frequency range.

11. The image forming apparatus according to claim 9, further comprising:
a correction adjustment module to determine a correction adjustment parameter based on the determination of the second detection module.

12. The image forming apparatus according to claim 11, wherein the first detection module determines the amount of VOC in a form of gas in the path of the detection signal based on an adjusted first signal formed by application of the correction adjustment parameter to the first signal.

13. The image forming apparatus according to claim 9, further comprising:
a beam splitter disposed inside the integrated detection housing unit to direct the detection signal emitted from the source module to the first filter and the second filter.

14. A method of detecting volatile organic compounds, the method comprising:
emitting a detection signal by a source module through a source window member thereof;
receiving the detection signal to determine an amount of volatile organic compounds (VOC) present in the path of the detection signal between the source module and the first detection module by a first detection module spaced apart from the source module through a first detection window member thereof; and
receiving the detection signal to determine deposit formation of the VOC on the source window member and the second detection window member by a second detection module spaced apart from the source module through a second detection window member thereof.

15. The method according to claim 14, further comprising:
filtering the detection signal by a first filter of the first detection module to output a first signal having a first predetermined frequency range corresponding to the amount of the VOC present in the path of the detection signal and the amount of deposit formation of the VOC on the source window member and the first detection window member;
filtering the detection signal by a second filter of the second detection module to output a second signal having a second predetermined frequency range corresponding to the amount of deposit formation of the VOC on the source window member and the second detection window member;
determining a correction adjustment parameter by a correction adjustment module based on the determination of the second detection module; and
determining the amount of VOC in a form of gas in the path of the detection signal by the first detection module based on an adjusted first signal formed by application of the correction adjustment parameter to the first signal.

16. An optical sensor system, comprising:
a source module including a source housing unit having a source window member, the source module to emit a detection signal through the source window member;
an integrated detection housing unit including a first detection module, a first filter, a second detection module, a second filter and a common detection window member spaced apart from the source module to pass through the detection signal to the first detection module through the first filter and the second detection module through the second filter;
the first filter to filter the detection signal and provide a first filtered signal to the first detection module;
the first detection module to determine an amount of volatile organic compounds (VOC) present in a path of the detection signal between the source module and the first detection module based on the first filtered signal,
the second filter to filter the detection signal and provide a second filtered signal to the second detection module; and
the second detection module to receive the detection signal to determine at least one of a presence and the amount of deposit formation of the VOC on the source window member and the second detection window member.

17. An optical sensor system, comprising:
a source module including a source housing unit having a source window member and a source shielding member, the source module to emit a detection signal through the source window member;
the source shielding member surrounding the source window member to reduce deposit formation of volatile organic compounds (VOC) on the source window member; and
a first detection module including a first detection housing unit having a first detection window member and a first detection shielding member, the first detection module spaced apart from the source module to receive the detection signal to determine an amount of the VOC present in a path of the detection signal between the source module and the first detection module;

the first detection shielding member surrounding the first detection window member to reduce deposit formation of the VOC on the first detection window member;

a second detection module including a second detection housing unit having a second detection window member and a second detection shielding member, the second detection unit spaced apart from the source module to receive the detection signal to determine at least one of a presence and an amount of deposit formation of the VOC on the source window member and the second detection window member;

the second detection shielding member surrounding the detection window member to reduce deposit formation of the VOC on the second detection window member; and a heating module to heat the source window member, the first detection window member, and the second detection window member to remove deposit formation of the VOC there from.

18. The optical sensor system according to claim 17, further comprising:

a first filter of the first detection module to filter the detection signal to output a first signal having a first predetermined frequency range corresponding to the amount of the VOC present in the path of the detection signal and the amount of deposit formation of the VOC on the source window member and the first detection window member;

a second filter of the second detection module to filter the detection signal to output a second signal having a second predetermined frequency range corresponding to the amount of deposit formation of the VOC on the source window member and the second detection window member; and a correction adjustment module to determine a correction adjustment parameter based on the determination of the second detection module; and wherein the first detection module determines the amount of VOC in a form of gas in the path of the detection signal based on an adjusted first signal formed by application of the correction adjustment parameter to the first signal.

19. The optical sensor system according to claim 18, wherein the first filter comprises a first narrow bandpass filter such that the first predetermined frequency range corresponds to a wavenumber range from 2800 $cm^{-1}$ to 3000 $cm^{-1}$ and the second filter comprises a second narrow bandpass filter such that the second predetermined frequency range corresponds to a wavenumber range outside the first predetermined frequency range.

20. The optical sensor system according to claim 17, further comprising:

a temperature detection unit to detect a respective temperature of the source window member, the first detection window member, and the second detection window member; and a control module to control the heating module based on at least one of a detection by the second detection module and a respective detection by the temperature detection unit.

* * * * *